US009299012B2

(12) United States Patent
Sato

(10) Patent No.: US 9,299,012 B2
(45) Date of Patent: Mar. 29, 2016

(54) CIGARETTE INSPECTION APPARATUS

(71) Applicant: JAPAN TOBACCO INC., Tokyo (JP)

(72) Inventor: Jun Sato, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 410 days.

(21) Appl. No.: 13/801,146

(22) Filed: Mar. 13, 2013

(65) Prior Publication Data

US 2013/0215259 A1     Aug. 22, 2013

Related U.S. Application Data

(63) Continuation of application No. PCT/JP2010/065792, filed on Sep. 14, 2010.

(51) Int. Cl.
*G06K 9/78* (2006.01)
*A24C 5/34* (2006.01)
*B65B 19/32* (2006.01)
(Continued)

(52) U.S. Cl.
CPC ............... *G06K 9/78* (2013.01); *A24C 5/3412* (2013.01); *B65B 19/32* (2013.01); *G01N 21/952* (2013.01); *G06K 9/00* (2013.01); *G06T 7/0006* (2013.01); *G06T 7/0008* (2013.01); *G06T 7/606* (2013.01); *G06K 2209/19* (2013.01); *G06T 2207/10024* (2013.01); *G06T 2207/20036* (2013.01);
(Continued)

(58) Field of Classification Search
CPC .... A24C 5/3412; B65B 19/32; G01N 21/952; G01N 21/8806; G06K 9/78; G06K 2209/19; G06K 9/00; G06T 2207/30164; G06T 7/0004; G06T 7/001; G06T 2207/10024; G06T 2207/20036; G06T 2207/30128; G06T 2207/30242; G06T 7/0006; G06T 7/0008; G06T 7/606; H04N 7/183
USPC ............................................................. 348/92
See application file for complete search history.

(56) References Cited

U.S. PATENT DOCUMENTS 3,722,172 A * 3/1973 Seragnoli .......................... 53/54
4,266,674 A * 5/1981 Bell et al. ...................... 209/536
(Continued)

FOREIGN PATENT DOCUMENTS

DE     196 42 793 A1    4/1998
JP     58-162281 A       9/1983
(Continued)

OTHER PUBLICATIONS

European Search Report dated Jun. 12, 2015 in related application No. 10857243.9 (7 pages).

*Primary Examiner* — Shan Elahi
(74) *Attorney, Agent, or Firm* — Birch, Stewart, Kolasch & Birch, LLP

(57) ABSTRACT

To analyze an inspection image obtained by taking an image of filter end faces of filter cigarettes horizontally arranged, from an axial direction, and thus inspect an excess cigarette feeding error, there are provided a first judging device that the number of cigarettes according to shape information of the filter end faces obtained from the inspection image, and a second judging device that obtains the centroid positions of the filter end faces from the inspection image, and detects that there is an excess feeding error when difference between a maximum value and a minimum value of the centroid-to-centroid distance of adjacent filter end faces is substantially equal to a previously-known diameter of the filter end face.

21 Claims, 9 Drawing Sheets

(51) Int. Cl.
*G01N 21/952* (2006.01)
*G06T 7/00* (2006.01)
*G06T 7/60* (2006.01)
*G06K 9/00* (2006.01)

(52) U.S. Cl.
CPC ............ *G06T2207/30128* (2013.01); *G06T 2207/30242* (2013.01)

(56) References Cited

U.S. PATENT DOCUMENTS

| | | | |
|---|---|---|---|
| 4,486,098 A | | 12/1984 | Buchegger et al. |
| 4,511,045 A | * | 4/1985 | Seragnoli .................... 209/535 |
| 4,612,803 A | * | 9/1986 | Manservisi et al. ............. 73/81 |
| 4,644,150 A | * | 2/1987 | Kuga et al. ............... 250/223 R |
| 4,693,374 A | * | 9/1987 | Dall'Osso .................... 209/535 |
| 4,899,889 A | * | 2/1990 | Gamberini et al. ........... 209/535 |
| 4,916,883 A | * | 4/1990 | Focke .............................. 53/53 |
| 4,955,948 A | | 9/1990 | Focke et al. |
| 5,392,359 A | * | 2/1995 | Futamura et al. ............. 382/141 |
| 5,979,140 A | | 11/1999 | Focke et al. |
| 6,373,519 B1 | * | 4/2002 | Sybert et al. .................... 348/86 |
| 6,373,520 B1 | * | 4/2002 | Cadieux et al. ................. 348/86 |
| 6,531,693 B1 | * | 3/2003 | Focke et al. .................... 250/221 |
| 7,779,846 B2 | * | 8/2010 | Spatafora et al. ............. 131/280 |
| 2002/0144540 A1 | * | 10/2002 | Rizzoli et al. .................... 73/37 |
| 2007/0295624 A1 | * | 12/2007 | Ancona et al. ................ 206/256 |
| 2009/0139534 A1 | * | 6/2009 | Saoud et al. ................... 131/284 |
| 2009/0159472 A1 | * | 6/2009 | Bardet .......................... 206/256 |
| 2010/0260378 A1 | * | 10/2010 | Noy et al. ..................... 382/103 |

FOREIGN PATENT DOCUMENTS

| | | |
|---|---|---|
| JP | 59-232085 A | 12/1984 |
| JP | 2-69172 A | 3/1990 |
| JP | 2001-524425 A | 12/2001 |
| JP | 3437753 B2 | 8/2003 |
| WO | 99/28190 A1 | 6/1999 |

* cited by examiner $$[d_{max} - d_{min}] \fallingdotseq \phi \ ?$$

CIGARETTE INSPECTION APPARATUS

CROSS-REFERENCE TO RELATED APPLICATIONS

This application is a Continuation of PCT International Application No. PCT/JP2010/065792 filed on Sep. 14, 2010. The entire contents of the above application are hereby expressly incorporated by reference.

TECHNICAL FIELD

The invention relates to a cigarette inspection apparatus capable of detecting an excess cigarette feeding error without fail from an inspection image of a filter-side face of a cigarette bundle containing filter cigarettes coaxially and horizontally arranged, which was taken from the axial direction of the cigarettes.

BACKGROUND ART

Filter cigarettes are wrapped with a predetermined number (twenty, for example) in each pack by means of a wrapping machine as disclosed in Patent Document 1, and are thus produced as tobacco packs. The wrapping machine disclosed in Patent Document 1 winds a wrapping material around the outer periphery of a bundle of filter cigarettes coaxially and horizontally arranged and stacked in multiple tiers, and folds both open ends of the wrapping material inwards to close and seal the ends, to thereby wrap the cigarette bundle.

PRIOR ART DOCUMENT

Patent Document

Patent Document 1: Japanese Patent No. 3437753

SUMMARY OF THE INVENTION

Problems to be Solved by the Invention

A tobacco pack of twenty cigarettes is generally produced by feeding the wrapping machine with a cigarette bundle in which filter cigarettes are horizontally arranged in three tiers of seven, six, and seven cigarettes, and wrapping a predetermined wrapping material. In rare cases, a cigarette bundle C containing 21 cigarettes is fed to a mandrel of the wrapping machine. More specifically, there is a case in which a middle tier includes seven cigarettes, and the bundle contains one more cigarette than a predetermined number. Such an excess cigarette feeding error might lead to a problem with the wrapping of the cigarette bundle or the problem that the wrapping crushes the cigarettes from their outer periphery.

In another case, when a bundle of cigarettes horizontally arranged and stacked in tiers is pushed into the mandrel of the wrapping machine in the axial direction of the cigarettes to be wrapped, the cigarettes located at the ends of the bundle might be broken, and filters might come off. It is important to remove (eliminate) the cigarette bundle with such an excess cigarette feeding error from the wrapping machine before wrapping the subject bundle, and thus retain a manufacturing quality as tobacco packs.

The invention has been made in light of the foregoing circumstances. It is an object of the invention to provide a cigarette inspection apparatus that optically detects a cigarette bundle that is fed to a wrapping machine, the bundle having an excess cigarette feeding error, which contains more cigarettes than the predetermined number, and reliably eliminates the cigarette bundle before the bundle is wrapped.

Means to Solving the Problem

In order to accomplish the above-mentioned object, the cigarette inspection apparatus takes an image of a filter-side face of a bundle of filter cigarettes coaxially and horizontally arranged from an axial direction of the cigarettes with camera, analyzes an inspection image, and thus inspects an excess cigarette feeding error, characterized by having:

a first judging device that detects the number of the filter cigarettes horizontally arranged on the basis of information about the shape of each of the filter end faces, which is obtained from the inspection image, and makes a judgment as to whether or not a detected number is equal to a predetermined number; and a second judging device that finds a centroid position of each of the filter end faces from the inspection image, compares distance between centroid points of every two adjacent filter end faces, and thus makes a judgment as to whether or not the filter cigarettes horizontally arranged are arranged at predetermined intervals.

Preferably, when difference between a maximum value and a minimum value of the distance between centroid points is substantially equal to a previously-known diameter of the filter end face, the second judging device detects that there is an excess feeding error.

When the cigarette bundle is formed by stacking, in a staggered manner, cigarette rows each containing n filter cigarettes coaxially and horizontally arranged and cigarette rows each containing (n−1) filter cigarettes coaxially and horizontally arranged, the second judging device carries out a process of detecting an excess feeding error with respect to the cigarette row in which the (n−1) filter cigarettes are arranged.

The second judging device is only required to carry out the process of detecting an excess feeding error in parallel with the first judging device or if there is no excess cigarette feeding error detected by the first judging device.

The cigarette inspection apparatus of the invention is characterized by having a third judging device that includes an inspection window smaller than the filter-side face of the cigarettes, which is set close to each end of an area in the inspection image, within which the predetermined number of cigarettes are expected to be horizontally arranged, obtains color information of the inside of the inspection window, and detects that there is an excess feeding error when the color information indicates a color of the filters.

Preferably, the third judging device is only required to carry out the process of detecting an excess feeding error in parallel with the first and second judging devices or if there is no excess cigarette feeding error detected by the first and second judging devices.

The cigarette inspection apparatus may also be constructed of the first and third judging devices.

When the cigarette bundle is formed by stacking, in a staggered manner, cigarette rows each containing n filter cigarettes coaxially and horizontally arranged and cigarette rows each containing (n−1) filter cigarettes coaxially and horizontally arranged, the third judging device carries out a process of detecting an excess feeding error with respect to the cigarette row in which the (n−1) filter cigarettes are arranged.

The third judging device is only required to carry out the process of detecting an excess feeding error in parallel with the first judging device or if there is no excess cigarette feeding error detected by the first judging device.

Another cigarette inspection apparatus of the invention takes an image of a filter-side face of a cigarette bundle formed by stacking, in a staggered manner, cigarette rows each containing n filter cigarettes coaxially and horizontally arranged and cigarette rows each containing (n−1) filter cigarettes coaxially and horizontally arranged, from an axial direction of the cigarettes with camera, analyzes an inspection image, and thus inspects an excess cigarette feeding error, having:

a first judging device that detects the number of the filter cigarettes of each of the cigarette rows on the basis of information about the shape of the filter end face, which is obtained from the inspection image, and judges that there is an excess feeding error when more cigarettes than a predetermined number are detected with respect to any one of the cigarette rows; and a fourth judging device that finds from the inspection image centroid positions of endmost filter end faces of the cigarette row in which the n cigarettes are arranged and centroid positions of the filter end faces inwardly adjacent to the endmost filter end faces, finds a centroid position of a filter end face located at each end of a cigarette row in which the (n−1) cigarettes are arranged, judges a distance difference of these centroid positions, and judges that the cigarette row of the (n−1) cigarettes has an excess feeding error when the distance difference is large.

Preferably, the fourth judging device is only required to carry out the process of detecting an excess feeding error in parallel with the first judging device or if there is no excess cigarette feeding error detected by the first judging device.

Also preferably, the cigarette inspection apparatus has the second or third judging device. The fourth judging device only have to be so configured as to carry out the process of detecting an excess feeding error in parallel with the first, second or third judging device or if there is no excess cigarette feeding error detected by the first, second or third judging device.

Preferably, the cigarette inspection apparatus of the invention has all the first to fourth judging devices.

In this case, too, the fourth judging device is only required to carry out the process of detecting an excess feeding error in parallel with the first to third judging devices or if there is no excess feeding error detected by the first to third judging devices.

The fourth judging device is desirably obtains a first line segment connecting centroid positions of endmost filter end faces of two cigarette rows in which n cigarettes are arranged in staggered rows with a cigarette row in which the (n−1) cigarettes are arranged intervening therebetween and a second line segment connecting centroid positions of filter end faces inwardly adjacent to the endmost filter end faces, and then obtains a distance difference between the first and second line segments and the centroid positions of the filter end faces located at both the ends of the (n−1) cigarette row, as a distance difference component in a direction of arrangement of the cigarettes between the centroid positions of the filter end faces.

Advantageous Effects of the Invention

The cigarette inspection apparatus of the invention not only obtains the shape of the filter-side face and inspects the number of cigarettes from the inspection image of the filter-side face of the cigarette bundle but also obtains the centroid positions of the filter end faces from the inspection image, and it is judged whether or not the filter cigarettes horizontally arranged are arranged at the predetermined intervals. The cigarette inspection apparatus is therefore capable of reliably detecting an excess cigarette feeding error. In particular, if a cigarette bundle passes the inspection of the number of cigarettes based upon the shape of the filter-side face, a cigarette arrangement condition is judged from arrangement intervals obtained from the centroid position of the filter section. It is then possible to reliably detect a cigarette excessive feeding error.

Based upon the color information in the area where there is supposed to be no cigarette, the presence of a filter in the area is detected, and thus, the cigarette arrangement condition is judged. It is therefore possible to reliably detect a cigarette excess feeding error.

In particular, when the cigarette bundle is formed by alternately stacking in staggered rows cigarette rows each in which the n filter cigarettes are horizontally arranged and cigarette rows each in which the (n−1) filter cigarettes are horizontally arranged, even if an excess cigarette feeding occasionally occurs, the excess cigarette feeding is seen mainly in the (n−1) cigarette row. Focusing on this fact, the invention subjects only the (n−1) cigarette row to the process of judging the excess cigarette feeding, which makes the process easy and efficient.

Concerning the judgment process, for example, an image of the filter-side face of a cigarette bundle that is fed to the wrapping machine is taken, and the inspection image used to judge whether there is a stain in the filter face or the like can be used. This provides the advantage that the cigarette inspection apparatus with high reliability in error detection can be materialized without difficulty, and the like.

MODE FOR CARRYING OUT THE INVENTION

A cigarette inspection apparatus of one embodiment of the present invention will be described below in detail with reference to the attached drawings.

The cigarette inspection apparatus inspects the presence/absence of an abnormal cigarette feeding, that is, an excess feeding error, with respect to each cigarette bundle, for example, containing a predetermined number of filter cigarettes arranged in a horizontal manner and then fed to and wrapped by a wrapping machine. The inspection is conducted through the steps of wrapping the cigarette bundle with a predetermined wrapping material by means of the wrapping machine, and analyzing an inspection image gained by taking an image of a filter-side face of the cigarette bundle before closing and sealing the wrapping material.

Descriptions thereof will be omitted in this specification. The image (inspection image) of the filter-side face of the cigarette bundle, which is taken by the wrapping machine, is used to inspect whether there is a stain in a filter end face of each cigarette before the bundle is wrapped, and to inspect where there is an axial deviation of cigarettes in the cigarette bundle, which are coaxially and horizontally arranged, that is, whether there is a protrusion of a cigarette from the filter-side face functioning as the basis for deviation.

A cigarette inspection apparatus installed in a wrapping machine will be used here to describe the invention. The cigarette inspection apparatus may also be installed in a manufacturing line in which filter cigarettes sequentially produced by means of a cigarette-making machine and a tip mounting device are delivered to the next section in bundles each containing a predetermined number of cigarettes.

Figure 1:
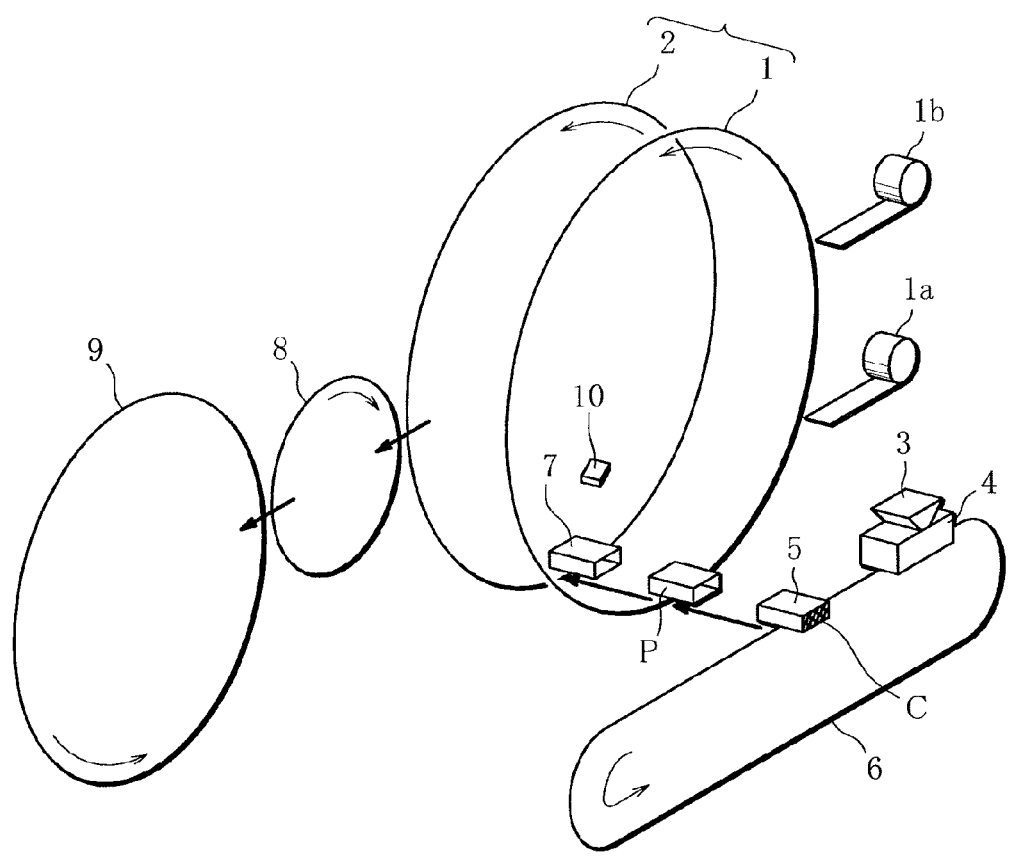
FIG. 1 is a schematic configuration view of a tobacco pack wrapping machine in which a cigarette inspection apparatus of the present invention is installed.

The cigarette wrapping machine, into which the cigarette inspection apparatus of the invention is installed, is constructed, for example, of the elements introduced in detail in the Patent Document 1. As illustrated in FIG. 1, the wrapping machine is provided mainly with a forming turret 1 that shapes a predetermined wrapping material into a bottomed square tube and a sealing turret 2 that is coaxially juxtaposed to the forming turret 1. The sealing turret 2 inserts a plurality of (twenty, for example) cigarettes horizontally arranged in the bottomed square tube-like wrapping material that is fabricated by the forming turret 1, and folds an open end of the wrapping material inwards to seal the wrapping material.

Figure 2:
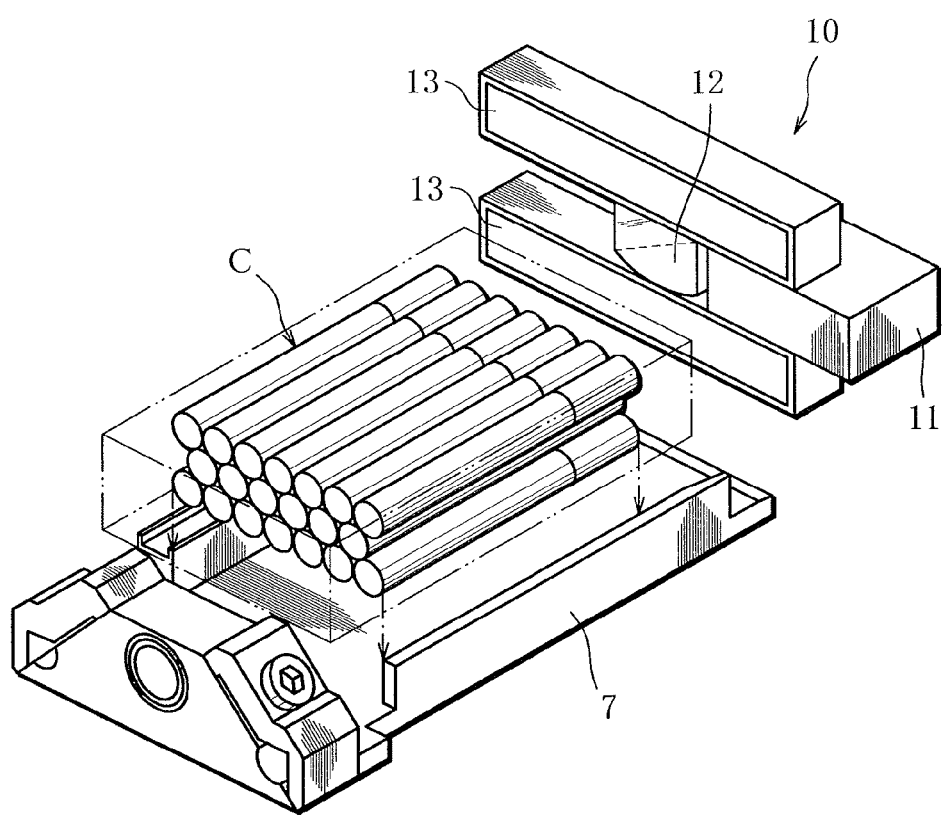
FIG. 2 is a view showing a bundle of filter cigarettes fed to the tobacco pack wrapping machine and a relation between the bundle and a camera for taking an image of a filter-side face of the bundle.

A bundle of cigarettes is formed by an alignment device 4 in which the filter cigarettes that are fed to a hopper 3 with filters facing in the same direction are horizontally stacked in three tiers including a top row of seven cigarettes, a middle row of six cigarettes, and a bottom row of seven cigarettes. The bundle is then put into a delivery pocket 5 and delivered to the forming turret 1 through a chain conveyor 6. A cigarette bundle C is pushed out of the delivery pocket 5 by a plunger, not shown, and enclosed in a bottomed square tube-like wrapping material P that is formed by the forming turret 1. The cigarette bundle C is then transferred with the bottomed square tube-like wrapping material P into a mandrel 7, for example as shown in FIG. 2, which is provided in the sealing turret 2.

The sealing turret 2 rotates to turn the mandrel 7 and thus folds an open end of the bottomed square tube-like wrapping material P containing the cigarette bundle C. By so doing, the sealing turret 2 seals the wrapping material P and wraps the cigarette bundle C. A tobacco pack in which the cigarette bundle C is enclosed is delivered from the sealing turret 2 to a delivery turret 8 and then guided to a drying turret 9. At the drying turret 9, the tobacco pack is subjected to a drying treatment and then put out into the market as a product.

Reference marks 1a and 1b in FIG. 1 are wrapping-material feeders that are placed along a circumferential orbit of the forming turret 1 and feed an inner packing material Pa made of an aluminum evaporated sheet and an outer packing material Pb made of a paper sheet, respectively, to a wrapping mandrel of the forming turret 1. The inner and outer packing materials Pa and Pb are superimposed upon each other and wound around the wrapping mandrel, thereby forming the bottomed square tube-like wrapping material P.

With respect to the cigarette wrapping machine basically configured as described above, a camera 10 of the cigarette inspection apparatus of the invention, which takes an image of the filter-side face of the cigarette bundle C, is situated at the side of the circumferential orbit of the sealing turret 2. In particular, the camera 10 is a so-called ultraminiature wide angle camera and fixed slightly downstream from where the mandrel 7 receives the cigarette bundle C and the wrapping material P. Before the open end of the wrapping material P is folded, that is, before the cigarette bundle C is sealed in the wrapping material P, the camera 10 takes an image of the filter-side face of the cigarette bundle C.

More specifically, the camera 10 is a so-called side view camera with a small width, which uses an optical system 12, such as a prism mounted on a front face of a camera body 11 as shown in FIG. 2, to take an image in a lateral direction of the camera body 11. The camera body 11 is provided with a so-called wide-angle lens having a lens radius of, for example, approximately 12 mm, and designed to image all filter end faces of cigarettes of the bundle C collectively from a position close to the filter end faces.

Disposed above and below the camera body 11 are strobes 13 that illuminate in the direction of taking an image. The strobes 13 are of a compact size and uses, for example, LED as a luminescent material. The use of a compact (ultracompact) camera as the camera 10 allows the camera 10 to be installed close to a lateral portion of the sealing turret 2. This way, the entire filter-side face of the cigarette bundle C that is fed to the mandrel 7 of the sealing turret 2 is imaged with the camera 10 before being sealed with the wrapping material P.

Figure 3:
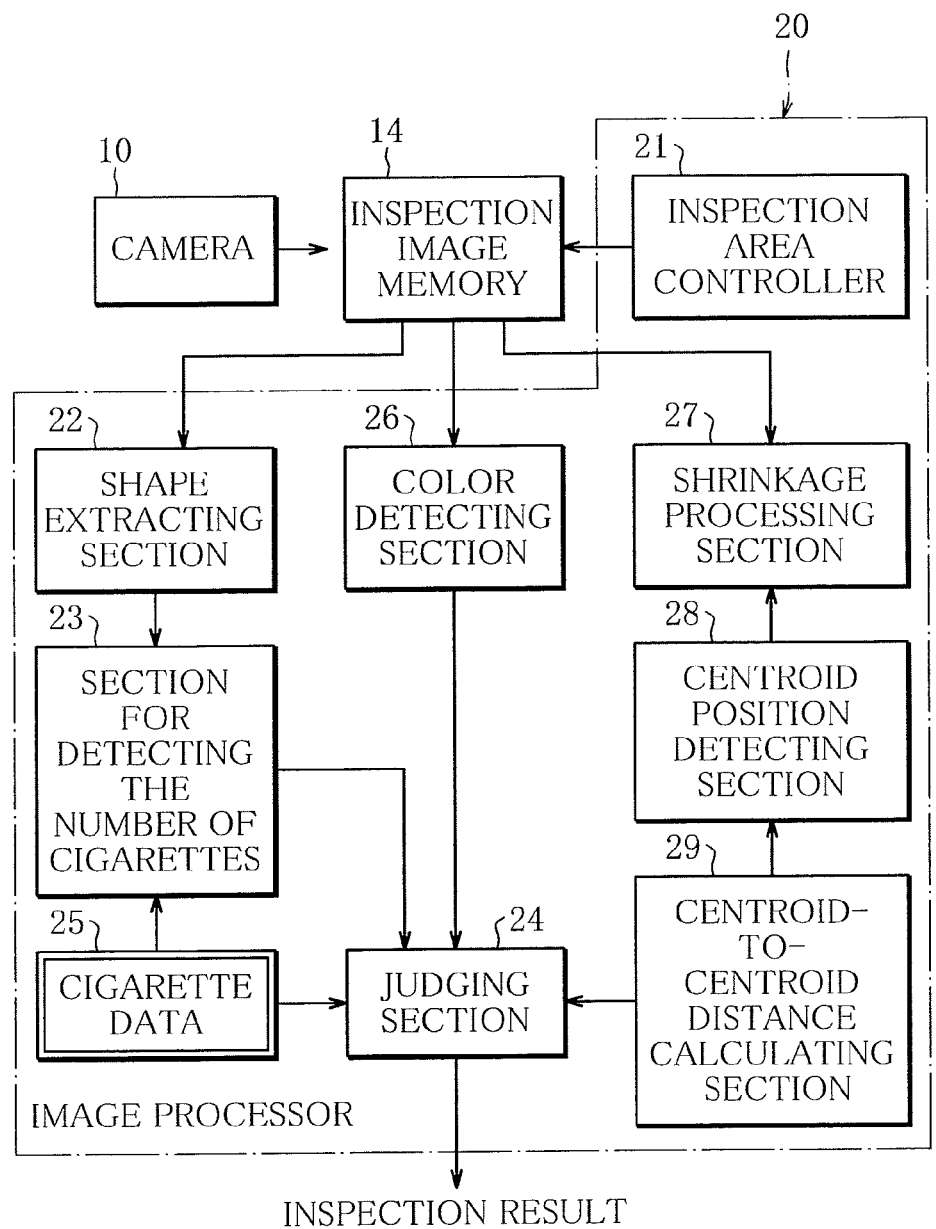
FIG. 3 is a schematic configuration view of a cigarette inspection apparatus according to one embodiment of the invention.
Figure 4:
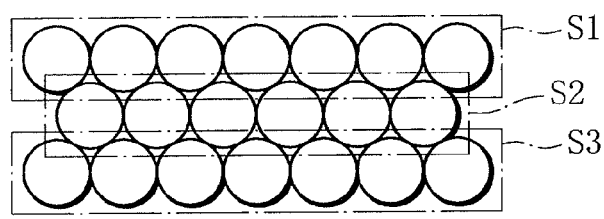
FIG. 4 is a view showing an example of search areas that are set in an inspection image.

FIG. 3 shows a schematic configuration of the cigarette inspection apparatus according to one embodiment of the invention. The cigarette inspection apparatus includes an inspection image memory 14 that stores inspection images including the filter-side face of the cigarette bundle C, which is imaged with the camera 10, and an image processor 20 that analyzes the inspection image (image of the filter-side face of the cigarette bundle C) stored in the inspection image memory 14. The image processor 20 is made of a microprocessor that analyzes the inspection image, for example, according to a preset program. The filter end faces of cigarettes in the inspection image if the cigarette bundle C, which are imaged with the camera 10, form bright areas that is illuminated with the strobes 13, whereas gaps among cigarettes and lateral portions of cigarettes form dark areas as they do not reflect illuminating lights.

The image processor 20 subjects the inspection image, for example, to a shape information extracting process, a color detecting process, and a process of detecting the centroid positions of the filter end faces as described below. The image processor 20 thus inspects whether the cigarette bundle C contains cigarettes horizontally stacked in three tiers including the top row of seven cigarettes, the middle row of six cigarettes, and the bottom row of seven cigarettes. An excess cigarette feeding error is likely to occur exclusively in the middle cigarette row, so that the image processor 20 judges the presence/absence of the excess feeding error mainly with respect to the middle cigarette row. To be more specific, the image processor 20 inspects whether seven cigarettes are arranged in the middle row of the cigarette bundle C, that is, whether one more than the correct number of cigarettes is excessively arranged (fed) in the middle row.

In order to conduct the foregoing inspection, the image processor 20 has an inspection area controller 21 that selectively reads out an image of a to-be-inspected area from the inspection image memory 14. To-be-inspected areas determined by the inspection area controller 21 are set as search areas S1, S2 and S3 in the inspection image, for specifying the filter end faces in the three cigarette rows in which cigarettes are stacked in tiers including the top row having seven cigarettes, the middle row having six cigarettes, and the bottom row having seven cigarettes, so as to be coaxially and horizontally arranged in each row. As mentioned below, the inspection area controller 21 also functions to set inspection windows w smaller than the filter end face of each cigarette in an area where no cigarette is supposed to be present, which is close to both ends of an area in which six cigarettes are expected to be horizontally arranged, in the middle cigarette row.

In the image processor 20, a shape information extracting section 22 detects the shapes of the filter end faces in each of the search areas S1, S2 and S3 in the inspection image, and a section for detecting the number of cigarettes 23 detects judges lines of the cigarettes shown as the shapes of the filter end faces and detects the number of cigarettes arranged in lines. More specifically, the shape information extracting section 22 obtains the shapes of the filter end faces of top, middle and bottom cigarette rows, which are cut out from the inspection image with respect to each of the search areas S1, S2 and S3. The section for detecting the number of cigarettes 23 checks the number of attached portions in the shapes of the filter end faces, which are generally obtained as a circle with a prescribed diameter, and thus obtains the number of cigarettes forming each of the cigarette rows.

The number of cigarettes forming each of the top, middle and bottom cigarette rows, which is detected from each of the search areas S1, S2 and S3, is transmitted to a judging section 24. The judging section 24 judges whether there is an excess cigarette feeding error. For example, if it is detected that the number of cigarettes in the middle tier is seven, and there are 21 cigarettes in total, the judging section 24 immediately judges that there is an excess feeding error. This process may be carried out with respect only to the middle cigarette row since the excess cigarette feeding error is likely to occur only in the middle cigarette row as mentioned above. The judging process described above makes up a first judging device of the present invention.

The image processor 20 has a color detecting section 26 that detects the color information of the inspection windows w. The inspection windows w are set in the minute areas located close to both the ends of the middle cigarette row in which six cigarettes are horizontally arranged, that is, the area in which no cigarette is supposed to be present, in the middle cigarette row as described above. If the middle cigarette row contains six cigarettes, color components of the inspection windows w are detected as dark portions (black in general) that are background portions of the cigarette bundle C. However, if the middle cigarette row contains seven cigarettes, the filters of the cigarettes located at both ends of the cigarette row coincide with the inspection windows w. As a result, the color components of the inspection windows w are detected as a filter color (white in general).

The color components of the inspection windows w, which are thus detected by the color detecting section 26, are transmitted to the judging section 24. On the basis of cigarette data about the cigarette bundle C, which is previously set in the memory 25, the judging section 24 makes a judgment from the color components as to whether there is any cigarette located in the areas of the inspection windows w, or more specifically, whether more than six cigarettes are arranged in the middle tier. If the color of the inspection windows w is the filter color, the judging section 24 immediately judges that there is an excess feeding error. The judging process described above makes up a third judging device of the present invention.

The image processor 20 further has a shrinkage processing section 27 that subjects the entire inspection image or each of the search areas S1, S2 and S3. The shrinkage processing is a preprocessing for detecting the centroid positions of the filter end faces in the cigarette bundle C and functions to shrink (lessen) the image areas of the end faces of the cigarettes individually.

Figure 5:
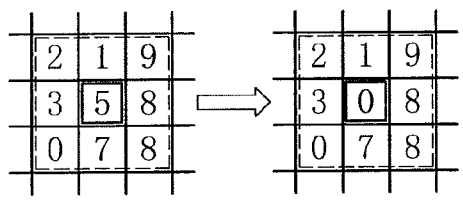
FIG. 5 is a view showing a concept of shrinkage processing with respect to an image.

More specifically, the shrinkage processing includes the steps of searching the inspection image or the images of the search areas S1, S2 and S3 with respect to each pixel in order; checking pixel values (brightness as image components), for example, of a pixel at a search position and other pixels encircling this particular pixel, or more specifically, "3×3" pixels as shown in FIG. 5; and replacing a pixel value that is the lowest value among the "3×3" pixels (value that is low in brightness) with a value of the pixel at the search position. The explanation will be provided on the premise that the brighter (whiter) the image information is, the higher the pixel value becomes. The darker (blacker) the image information is, the lower the pixel value becomes. In other words, the shrinkage processing searches the inspection image or the images of the search areas with respect to each pixel in order, and replaces the value of a target pixel with a value of the pixel that is lowest in value among the pixels encircling the target pixel, thereby smoothening the target pixel into the background, and shrinking the images of the search areas.

For example, tones of an image are represented on a scale of zero to nine, in which white is a pixel value "9", and black is "0". If the values of the "3×3" pixels consisting of the target pixel and the encircling pixels are 2, 1, 9, 3, 5, 8, 0, 7 and 9 in the order named from top left as shown in FIG. 5, the target pixel's value "5" is replaced with the pixel value "0" that is a minimum value among the encircling pixels. In this manner, the value of a target pixel is replaced with the value of one of the encircling pixels, which is the lowest in brightness, and the same process is repeated. Consequently, a peripheral part of the image of the filter portion that is high in brightness is gradually replaced with the brightness of the background portion, so that the images (filter images) of the search areas are shrunk. If the target pixel is replaced with a maximum pixel value, instead of the minimum pixel value among the values of the encircling pixels, the images (filter images) of the search areas are expanded.

Figure 6:
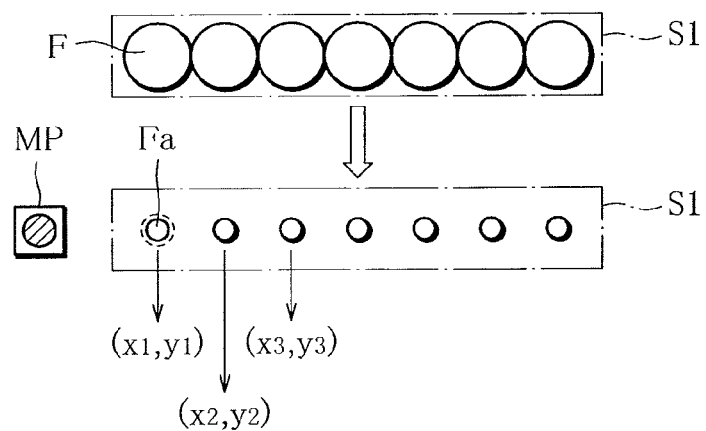
FIG. 6 is a view showing an example of detection of centroid positions of filter end faces from an image that has been subjected to shrinkage processing.

The shrinkage processing is repeated with respect, for example, to each of the search areas S1, S2 and S3 until an image portion F of the filter end face in the inspection image is shrunk to a prescribed size. As a result, the image portion F of the filter end face in the search areas S1, S2 and S3 is shrunk as shown in FIG. 6. A filter-end-face image (area with a high brightness) Fa that has been shrunk is cut away from filter-end-face images Fa of adjacent cigarettes. The shrinkage processing simply lessen the brightness of the peripheral part of the area with a high brightness according to the brightness of the background, so that the position (centroid position) as the image F showing the filter end faces of the search areas S1, S2 and S3 is not changed.

On the basis of the image subjected to the shrinkage processing as described, a centroid position detecting section 28 obtains the centroid positions of the cigarettes forming the filter-side face of the cigarette bundle C. The centroid position detection is conducted by carrying out a pattern matching processing using a mask pattern (standard pattern) MP of a prescribed size, for example, as shown in FIG. 6. The mask pattern MP used for the pattern matching is set, for example, as an image slightly larger than the filter-end-face image Fa obtained through the shrinkage processing. The centroid position detecting section 28 scans the search areas S1, S2 and S3 by using the mask pattern MP, and obtains a scanning position of the mask pattern when the filter-end-face image Fa is included in the mask pattern MP, as a centroid position [x, y] of the filter-end-face image Fa.

A centroid-to-centroid distance calculating section 29 included in the image processor 20 has a function to one-dimensionally obtain the centroid-to-centroid distance between cigarettes located especially in the middle cigarette row, which are adjacent to each other in a direction of the row, from the centroid position of the filter end face of each cigarette, which is obtained in the foregoing manner. the centroid-to-centroid distance calculating section 29 further has a function to evaluate a misalignment between the centroid positions with respect to the middle cigarette row, on the basis of the alignment of the cigarettes in the top and bottom cigarette rows arranged on and underneath the middle cigarette row. The centroid-to-centroid distance between the adjacent cigarettes in the middle cigarette row, which is obtained by the centroid-to-centroid distance calculating section 29 is transmitted to the judging section 24.

The judging section 24 then obtains a maximum value Dmax and a minimum value Dmin of a centroid-to-centroid distance D of the filter end faces in the middle cigarette row, and makes a judgment as to whether difference [Dmax−Dmin] is substantially equal to the previously-known filter diameter. If the difference [Dmax−Dmin] is substantially equal to the filter diameter, the judging section 24 detects that there is an error in the arrangement of the middle cigarette row. This judging process is carried out with respect especially to the cigarette bundle C that has passed the inspection on the number of cigarettes based upon the shape of the filters, or more specifically, the middle cigarette row in which the excess feeding error is likely to occur. The judging process based upon the centroid-to-centroid distance w of the filter end faces of the middle cigarette row makes up a second judging device of the present invention.

The centroid-to-centroid distance calculating section 29 has a function that uses as references the centroid positions of the endmost filter end faces of the top and bottom cigarette rows and the centroid positions of the filter end faces inwardly adjacent to the endmost filter end faces, and obtains a displacement of centroid positions of the endmost filter end faces of the middle cigarette row from the reference positions from the reference positions, on the basis of the centroid positions of the filter end faces of the cigarettes. The displacement may also be evaluated by obtaining distance between the centroid positions of the endmost filter end faces of the top and bottom cigarette rows and the centroid position of the endmost filter end face of the middle cigarette row, and distance between the centroid positions of the filter end faces inwardly adjacent to the endmost filter end faces and the centroid position of the end most filter end face of the middle cigarette row.

According to the present embodiment, however, the centroid-to-centroid distance calculating section 29 obtains, as a preprocessing, a first line segment L1 connecting the centroid positions of the endmost filter end faces in the top and bottom cigarette rows in which seven cigarettes are arranged and a second line segment L2 connecting the centroid positions of the filter end faces inwardly adjacent to the endmost filter end faces. The first and second line segments L1 and L2 serve as reference positions used to evaluate the locations of the cigarettes in the cigarette bundle C. The centroid-to-centroid distance calculating section 29 is designed to obtain difference in distance between the first and second line segments L1 and L2 and the centroid positions of the endmost filter end faces in the middle cigarette row in which six cigarettes are arranged, as a misalignment component of the centroid positions of the endmost filter end faces in the cigarette row of the middle tier in an arranging direction of the cigarettes.

From distance between the centroid positions of the endmost filter end faces in the middle cigarette row and the reference positions (first and second line segments L1 and L2) obtained from the positions of the filter end faces of the top and bottom cigarette rows, the judging section 24 judges a misalignment amount thereof. The judging section 24 makes a judgment from the misalignment amount as to whether there is an excess feeding error in the middle cigarette row as described below. The processing of judging an excess feeding error based upon the misalignment of the centroid positions of the filter end faces in the middle cigarette row in relation to the reference positions makes up a fourth judging device of the present invention.

Figure 7:
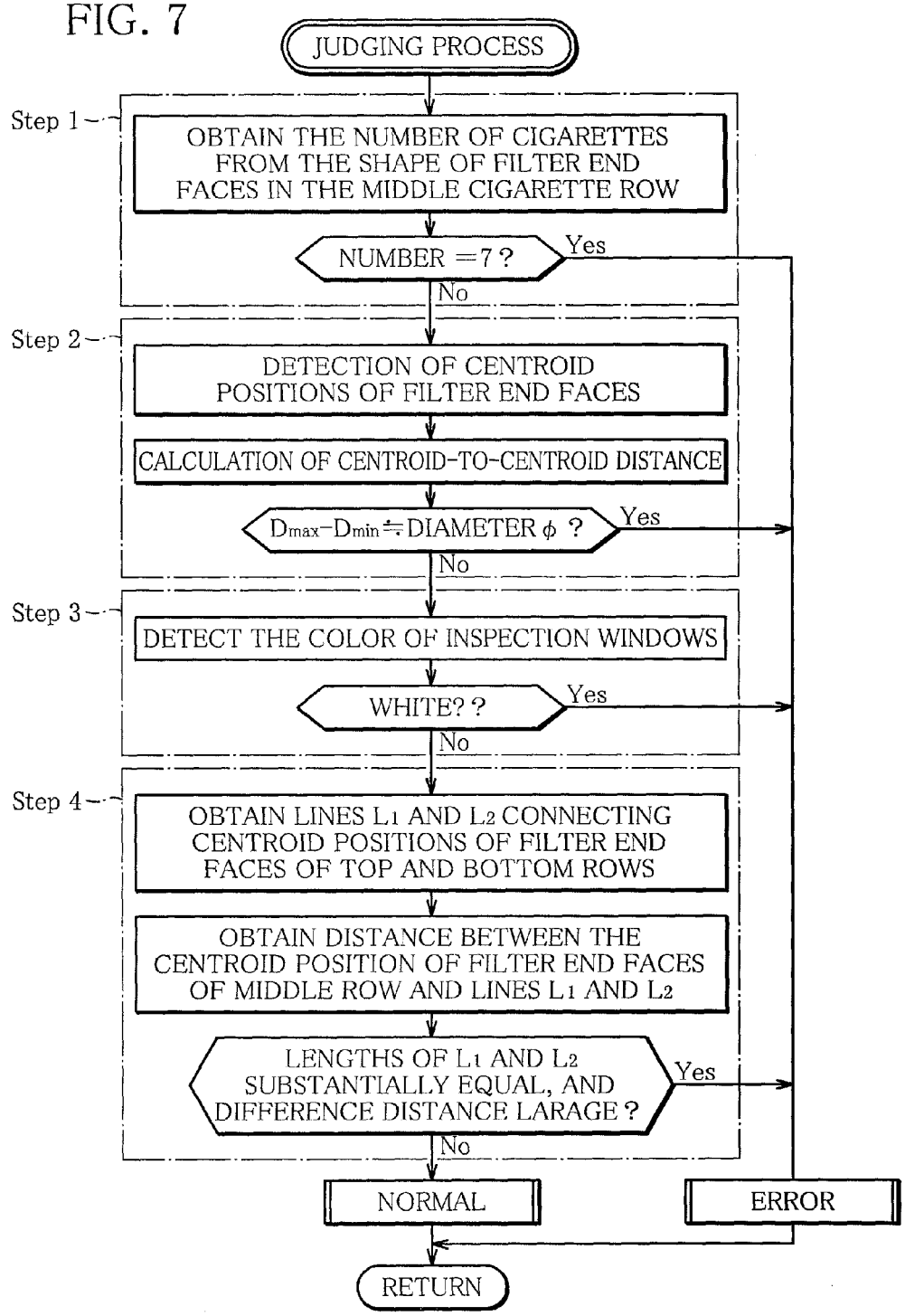
FIG. 7 is a view showing an example of a procedure of judging excess cigarette feeding according to the invention.

The description below is about basic judging steps (algorithm) of an excess cigarette feeding error in the cigarette inspection apparatus using the image processor 20 thus configured. This judging process basically includes four processing steps 1 to 4 as shown in FIG. 7. The processing steps 1 to 4 correspond to the first to fourth judging devices, respectively. In the cigarette bundle C containing cigarettes stacked in three tiers including the top row of seven cigarettes, the middle row of six cigarettes, and the bottom row of seven cigarettes horizontally arranged, in order to inspect an excess cigarette feeding that is likely to occur only in the middle cigarette row, the present embodiment conducts the inspection targeting the filter end faces of the middle cigarette row in the inspection image.

The judging process is started by checking the number of cigarettes (number of filter end faces), focusing on the shapes of the filter end faces in the middle cigarette row. If the number of cigarettes (number of filter end faces) is seven, which is one more than the predetermined number, it is judged that there is an excess feeding error (Step 1). However, even if the detected number of cigarettes (number of filter end faces) is six that is the predetermined number, it is not concluded that there is no error. This is because, if seven cigarettes are wedged into the middle tier, the filters of adjacent cigarettes are crushed against each other to be deformed, and there is the possibility that the shape inspection cannot be conducted. Or if wedged, the cigarettes might be broken and come off.

When the cigarette bundle C passes the inspection of the number of cigarettes (number of filter end faces), which is conducted by Step 1, the routine proceeds to Step 2, and Step 2 detects the centroid positions of the filter end faces in the middle cigarette row. The detection of the centroid positions is conducted after the filter-end-face image is subjected to the shrinkage processing. The filters of adjacent cigarettes are then crushed against each other to be deformed. It is then possible to separate and detect adjacent two filter end faces that cannot be judged from the shape and obtain the centroid positions thereof.

Figure 8:
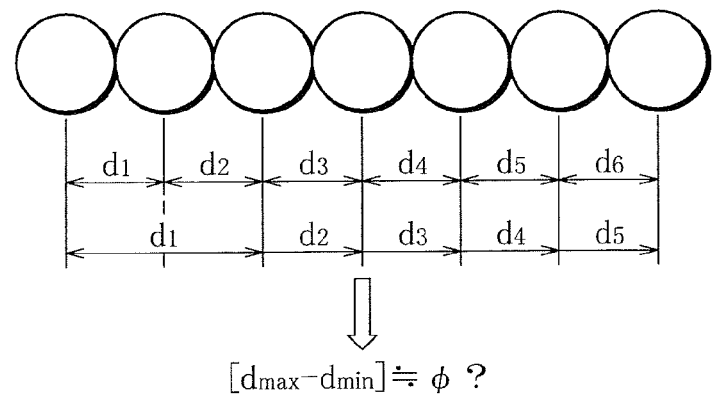
FIG. 8 is a view showing a concept of the procedure of judging the excess cigarette feeding on the basis of a centroid-to-centroid distance of the filter-side face.

It is also possible to find the number of cigarettes (number of filter end faces) in the middle cigarette row by checking the number of the centroid positions of the filter end faces, which are obtained in the foregoing manner. In the present embodiment, however, a centroid-to-centroid distance d between two adjacent filter end faces is calculated as shown in FIG. 8. A maximum value dmax and a minimum value dmin of the centroid-to-centroid distance are obtained, and it is judged whether difference [dmax−dmin] between the maximum dmax and the minimum value dmin is substantially equal to a filter diameter ϕ that is previously obtained (Step 2).

According to the judging process, the middle cigarette row contains six cigarettes that is the predetermined number. If the cigarettes are horizontally arranged in good order, the difference [dmax−dmin] between the maximum value dmax and the minimum value dmin is approximately zero. When the difference [dmax−dmin] is approximately equal to the filter diameter ϕ, it is indicated that one filter is missing in the cigarette row. Therefore, even if the number of cigarettes (number of filter end faces) is judged as six, it can be judged that there are actually seven cigarettes. In other words, it can be judged that the number of cigarettes in the middle cigarette row is seven that is one more than the predetermined number, namely, six.

On the other hand, it is impossible to detect the filters of the endmost cigarettes in the middle cigarette row from the inspection image. Consequently, if the centroid positions of the endmost filters cannot be detected, the difference [dmax−dmin] between the maximum value dmax and the minimum value dmin becomes approximately zero in Step 2. In this case, the excess feeding error cannot be detected in Step 2 even if the number of cigarettes in the middle cigarette row is seven that is one more than the predetermined number, namely, six. The routine then moves to Step 3.

Figure 9:
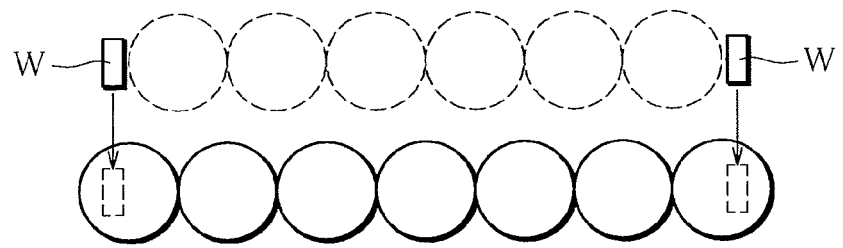
FIG. 9 is a view showing inspection windows w situated near both ends of a cigarette row and a concept of the procedure of judging an excess cigarette feeding error by detecting a color component.

As shown in FIG. 9, with respect to the middle cigarette row, Step 3 detects the color of the inspection windows w placed close to both the ends of the area in which six cigarettes are arranged. It is then judged whether the color is a preset filter color (white), or in other words, whether the color is dark (black) representing the background of the cigarette row. In this way, it is judged whether there are cigarettes in these places. As a result of the color judgment, even if it is impossible to detect the filters of the endmost cigarettes in the middle cigarette row, and furthermore, the centroid positions thereof, the presence/absence of cigarettes at both the ends can be checked. It is therefore possible to acquire the judgment result of Step 2.

However, if the filters of the endmost cigarettes in the middle tier are missing, an excess cigarette feeding error cannot be detected even by conducting the error judgment processing (Steps 1 to 3). The routine then moves to Step 4.

Step 4 uses the information about the centroid positions of the endmost filter end faces and those of the filter end faces inwardly adjacent to the endmost filter end faces in the top and bottom cigarette rows to evaluate the centroid positions of the endmost filters in the middle cigarette row, thus inspecting an excess feeding error in the middle cigarette row. In particular, Step 4 functions to conduct a final inspection of an excess feeding error with respect to a cigarette row C that has been judged to have no excess cigarette feeding error in Steps 1 to 3.

Figure 10:
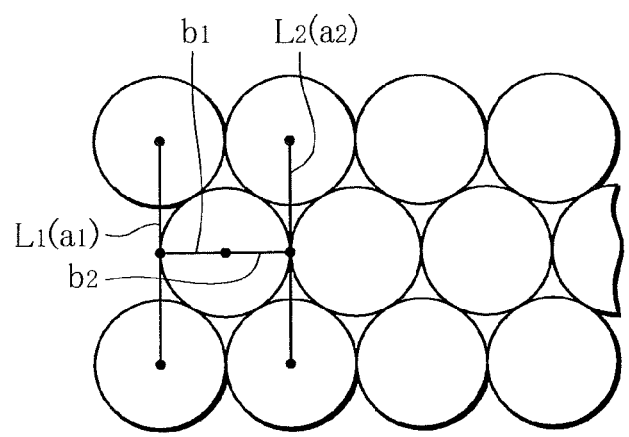
FIG. 10 is a view showing a concept of the procedure of judging an excess cigarette feeding error in a middle cigarette row by using the centroid positions of endmost filter end faces and those of filter end faces inwardly adjacent to the endmost filter end faces in top and bottom cigarette rows.

In other words, Step 4 first obtains the centroid positions of the filters located at both the ends of the top and bottom cigarette rows and the centroid positions of the filters inwardly adjacent to these endmost filters. As shown in FIG. 10, Step 44 then obtains the first line segment L1 connecting the centroid positions of the endmost filter end faces in the top and bottom cigarette rows and the second line segment L2 connecting the centroid positions of the filter end faces inwardly adjacent to the endmost filter end faces. The first and second line segments L1 and L2 are used as reference lines for evaluating the positions of the filter end faces of the endmost cigarettes in the middle cigarette row. At the same time, lengths a1 and a2 of the first and second line segments L1 and L2 are also obtained.

Thereafter, a centroid position G of the endmost filters in the middle cigarette row and distances b1 and b2 between the centroid position G and the first and second line segments L1 and L2 are obtained. Difference [b1−b2] between the distances b1 and b2 and difference [a1−a2] between the lengths a1 and a2 of the first and second line segments L1 and L2.

If the middle cigarette row contains six cigarettes, and these cigarettes are arranged in good order and stacked in tiers between top and bottom cigarette rows each containing seven cigarettes, the filter end faces of the endmost cigarettes in the middle tier are positioned at the center of the endmost filter end faces of the top and bottom cigarette rows and the filter end faces inwardly adjacent to the endmost filter end faces as shown in FIG. 10. The difference [b1−b2] between the distances b1 and b2 is therefore zero. In this case, the lengths a1 and a2 of the first and second line segments L1 and L2 are substantially equal to each other.

Figure 11:
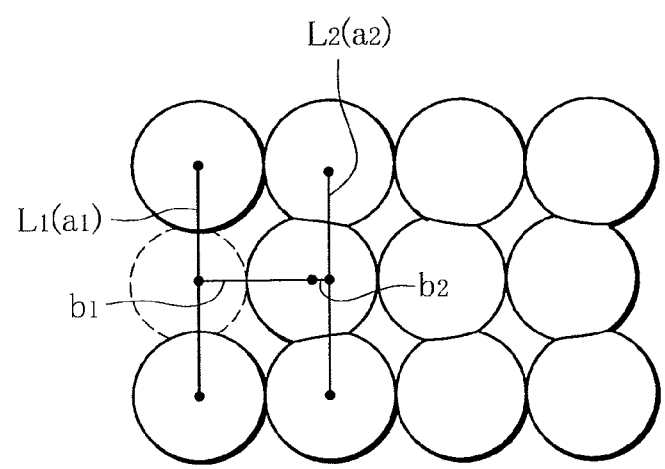
FIG. 11 is a view showing an evaluation example of centroid positions in a case where the filter of an endmost cigarette in the middle cigarette row is missing (fell off).

However, if the middle cigarette row contains seven cigarettes, and the filters of the endmost cigarettes are missing (come off), it is impossible to detect the filters of the endmost filters in the middle cigarette row as shown in FIG. 11. For that reason, the endmost filters in the middle cigarette row apparently belong to the cigarettes located inwardly adjacent to the endmost cigarettes. As shown in FIG. 11, therefore, there is a large difference between the centroid position G of the endmost filters in the middle cigarette row and the distances b1 and b2 between the line segments L1 and L2, and the difference [b1−b2] becomes large.

Figure 12:
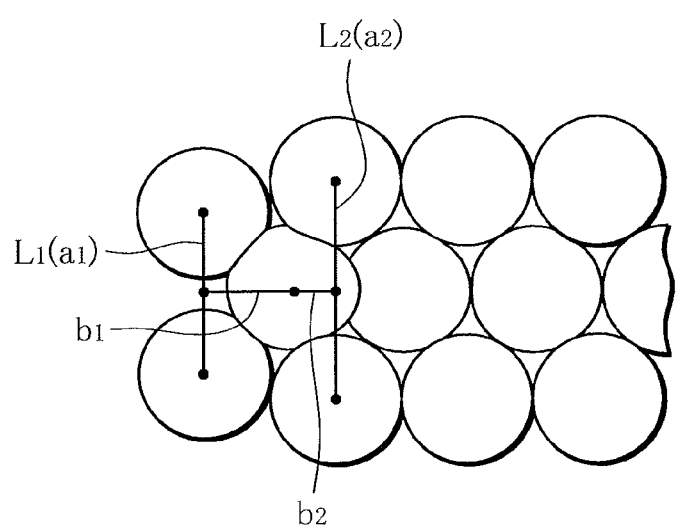
FIG. 12 is a view showing an evaluation example of centroid positions in a case where an endmost cigarette in the middle cigarette row is pushed by endmost cigarettes in the top and bottom cigarette rows and is displaced in position.

If the end of the cigarette bundle C is applied with external force and deformed, for example, as shown in FIG. 12, the endmost cigarette in the middle cigarette row is wedged inwards. This produces difference in the distances b1 and b2 between the centroid position G of the endmost filter in the middle cigarette row and the first and second line segments L1 and L2. In such a case, the lengths a1 and a2 of the first and second line segments L1 and L2 also differ from each other.

In light of the foregoing matter, the fourth judging process (Step 4) judges the difference [b1−b2] between the distances b1 and b2 and the difference [a1−a2] between the lengths a1 and a2 of the first and second line segments L1 and L2. Only if the lengths a1 and a2 of the first and second line segments L1 and L2 are substantially equal to each other, and the difference [b1−b2] in the distance b1 and b2 between the centroid position G and the first and second line segments L1 and L2 is larger than a predetermined threshold value, it is judged that there is an excess feeding error in the middle cigarette row. If it is judged in the judging processes (Steps 1 to 4) that no excess feeding error is found in the middle cigarette row, the judging section 24 obtains a judgment result that the cigarette bundle C contains the predetermined number of cigarettes, that is, that there is no excess feeding error (normal). On this account, even if the filter of the endmost cigarette in the middle cigarette row is missing (comes off), the excess feeding error can be detected without fail.

As described above, according to the cigarette inspection apparatus that inspects an excess feeding error in the cigarette bundle C, the inspection is focused particularly upon the middle cigarette row that is likely to have the excess feeding error. Even if no error is found in the number of filter end faces (number of cigarettes), which is detected from the shape information of the filter-end-face image, the inspection is focused upon the centroid positions of the filter end faces, and the number of cigarettes in the middle cigarette row is inspected. The inspection is enhanced in reliability. Furthermore, the presence/absence of an excess feeding error is inspected before cigarettes are wrapped, by using the inspection image of the filter-side face of the cigarette bundle C, so that it is easy to eliminate the cigarette bundle C having an excess feeding error from the wrapping machine according to the inspection result.

According to the above embodiment, the image processing is focused upon the middle cigarette row, which greatly reduces processing load, as compared to the image processing carried out with respect to the entire cigarette bundle. It is also possible to conduct the image processing and a stain inspection processing with respect to the filter end faces in parallel, and reduce time required for the judging process. In this view, the cigarette inspection apparatus is very advantageous in retaining a manufacturing quality of tobacco packs manufactured by wrapping cigarette bundles.

The present invention is not limited to the above-described embodiment. Although the embodiment shows the best example for enhancing the reliability of the inspection, the second judging process (Step 2) and the third judging process (Step 3) may be carried out in reverse order. Needless to say, if an excess cigarette feeding error is detected in the first to third judging processes (Step 1 to 3), the subsequent inspection processing may be omitted. Moreover, if a little deterioration in reliability of the inspection is allowed, the second to fourth judging processes (Step 2 to 4) may be selectively conducted after the first judging process (Step 1). In this case, the processing load can be greatly reduced. Furthermore, it is naturally possible to conduct Steps 1 to 4 in parallel, judge the results of the judgment comprehensively, and determine the presence/absence of an excess cigarette feeding error.

The embodiment has been described using the example of the inspection of the cigarette bundle C in which horizontally-arranged cigarettes are stacked in tiers including the top row of seven cigarettes, the middle row of six cigarettes, and the bottom row of seven cigarettes. However, the number of tiers and the number of cigarettes in each tier are not particularly limited. The inspection can be conducted in the same manner with respect to a ten-cigarette bundle in which cigarettes are horizontally arranged in two tiers each including five cigarettes. In this case, since the cigarettes are not stacked in tiers, the fourth judging device is unnecessary. The inspection is conducted with respect to each cigarette row by using the first to third judging devices. This type of tobacco package containing ten cigarettes is very unlikely to have an excess feeding error because the number of cigarettes of each row is set to be fixed. Therefore, the inspection requires only the above-described judging process. The invention may be modified in various ways without deviating from the gist thereof.

REFERENCE MARKS

10 Camera
13 Strobe
14 Inspection image memory
20 Image processor
21 Inspection area controller
22 Shape extracting section
23 Section for detecting the number of cigarettes
24 Judging section
25 Memory (cigarette data)
26 Color detecting section
27 Shrinkage processing section
28 Centroid position detecting section
29 Centroid-to-centroid distance calculating section

The invention claimed is:

1. A method for detecting an excess cigarette feeding error comprising the following steps:
   taking an inspection image of a filter end face of a bundle of filter cigarettes coaxially and horizontally arranged, from an axial direction of the cigarettes with a camera, and
   analyzing the inspection image, and further comprising:
   a first judging step comprising:
      detecting the number of the filter cigarettes horizontally arranged on the basis of information about the shape of each of the filter end faces, which is obtained from the inspection image, and
      making a judgment as to whether or not a detected number is equal to a predetermined number; and
   a second judging step comprising:
      finding a centroid position of each of the filter end faces from the inspection image,
      comparing a distance between centroid points of every two adjacent filter end faces, and
      making a judgment as to whether or not the filter cigarettes horizontally arranged are arranged at predetermined intervals.

2. The method according to claim 1, wherein when difference between a maximum value and a minimum value of the distance between centroid points is substantially equal to a previously-known diameter of the filter end face, it is detected in the second judging step that there is an excess feeding error.

3. The method according to claim 1, wherein the cigarette bundle is formed by stacking, in a staggered manner, cigarette rows each containing n filter cigarettes coaxially and horizontally arranged and cigarette rows each containing (n−1) filter cigarettes coaxially and horizontally arranged, and
   an excess feeding error with respect to the cigarette row in which the (n−1) filter cigarettes are arranged is detected in the second judging second judging step.

4. The method according to claim 1, wherein an excess feeding error is detected in the second judging step in parallel with the first judging step or if there is no excess cigarette feeding error detected in the first judging step.

5. The method according to claim 1, including:
   a third judging step comprising:
      obtaining color information on the inside of an inspection window smaller than the filter end face of the cigarettes, which is set close to each end of an area in the inspection image, within which the predetermined number of cigarettes are expected to be horizontally arranged, and
      judging that there is an excess feeding error when the color information indicates a color of the filters.

6. The method according to claim 5, wherein an excess feeding error is detected in the third judging step in parallel with the first and second judging steps or if there is no excess cigarette feeding error detected in the first and second judging steps.

7. A method for detecting an excess cigarette feeding error comprising the steps of:

taking an inspection image of a filter end face of a bundle of filter cigarettes coaxially and horizontally arranged, from an axial direction of the cigarettes with a camera, and analyzing the inspection image, and further comprising:

a first judging step comprising:
  detecting the number of the filter cigarettes horizontally arranged on the basis of information about the shape of each of the filter end faces, which is obtained from the inspection image, and
  making a judgment as to whether or not a detected number is equal to a predetermined number; and a third judging step comprising:
  obtaining color information of the inside of an inspection window smaller than the filter end face of the cigarettes, which is set close to each end of an area in the inspection image, within which the predetermined number of cigarettes are expected to be horizontally arranged, and
  judging that there is an excess feeding error when the color information indicates a color of the filters.

8. The method according to claim 7, wherein the cigarette bundle is formed by stacking, in a staggered manner, cigarette rows each containing n filter cigarettes coaxially and horizontally arranged and cigarette rows each containing (n−1) filter cigarettes coaxially and horizontally arranged, and
  an excess feeding error with respect to the cigarette row in which the (n−1) filter cigarettes are arranged is detected in the third judging step.

9. The method according to claim 7, wherein an excess feeding error is detected in the third judging step in parallel with the first judging step or if there is no excess cigarette feeding error detected in the first judging step.

10. A method for detecting an excess cigarette feeding error comprising the following steps:
  taking an inspection image of a filter end face of a cigarette bundle formed by stacking, in a staggered manner, cigarette rows each containing n filter cigarettes coaxially and horizontally arranged and cigarette rows each containing (n−1) filter cigarettes coaxially and horizontally arranged, from an axial direction of the cigarettes with a camera, and analyzing the inspection image, and further comprising:

a first judging step comprising:
  detecting the number of the filter cigarettes of each of the cigarette rows on the basis of information about the shape of the filter end face, which is obtained from the inspection image, and
  judging that there is an excess feeding error when more cigarettes than a predetermined number are detected with respect to any one of the cigarette rows; and a fourth judging step comprising:
  finding from the inspection image centroid positions of endmost filter end faces of the cigarette row in which the n cigarettes are arranged and centroid positions of the filter end faces inwardly adjacent to the endmost filter end faces,
  finding a centroid position of a filter end face located at each end of a cigarette row in which the (n−1) cigarettes are arranged,
  judging a distance difference of these centroid positions, and
  judging that the cigarette row of the (n−1) cigarettes has an excess feeding error when the distance difference is large.

11. The method according to claim 10, wherein an excess feeding error is detected in the fourth judging step in parallel with the first judging step or if there is no excess cigarette feeding error detected in the first judging step.

12. The method according to claim 10, wherein the fourth judging step comprising:
  obtaining a first line segment connecting centroid positions of endmost filter end faces of two cigarette rows in which n cigarettes are arranged in staggered rows with a cigarette row in which the (n−1) cigarettes are arranged intervening therebetween and a second line segment connecting centroid positions of filter end faces inwardly adjacent to the endmost filter end faces, and
  obtaining a distance difference between the first and second line segments and the centroid positions of the filter end faces located at both the ends of the (n−1) cigarette row, as a distance difference component in a direction of arrangement of the cigarettes between the centroid positions of the filter end faces.

13. A method for detecting an excess cigarette feeding error comprising the steps of:
  taking an inspection image of a filter end face of a cigarette bundle formed by stacking, in a staggered manner, cigarette rows each containing n filter cigarettes coaxially and horizontally arranged and cigarette rows each containing (n−1) filter cigarettes coaxially and horizontally arranged, from an axial direction of the cigarettes with a camera, and analyzing the inspection image, and further comprising:

a first judging step comprising:
  detecting the number of the filter cigarettes of each of the cigarette rows on the basis of information about the shape of the filter end face, which is obtained from the inspection image, and
  judging that there is an excess feeding error when it is detected that the number of the cigarettes is more than a predetermined number in any one of the cigarette rows;

a second judging step comprising:
  finding from the inspection image a centroid position of each of the filter end faces in the cigarette row containing the (n−1) cigarettes,
  obtaining centroid-to-centroid distance between adjacent filter end faces, and
  judging that there is an excess feeding error when difference between a maximum value and a minimum value of the centroid-to-centroid distance is substantially equal to a previously-known diameter of the filter end face; and a fourth judging step comprising:
  finding from the inspection image centroid positions of endmost filter end faces of the cigarette row containing the n cigarettes and centroid positions of the filter end faces inwardly adjacent to the endmost filter end faces,
  finding a centroid position of a filter end face located at each end of a cigarette row in which the (n−1) cigarettes are arranged,
  judging a distance difference of these centroid positions, and
  judging that the cigarette row of the (n−1) cigarettes has an excess feeding error when the distance difference is large,
  wherein the fourth judging step is performed when an excess feeding error is not detected in the second judging step.

14. The method according to claim 13, wherein an excess feeding error is detected in the fourth judging step in parallel with the first and second judging steps or if there is no excess cigarette feeding error detected in the first and second judging steps.

15. The method according to claim 13, wherein the fourth judging step comprising:
   obtaining a first line segment connecting centroid positions of endmost filter end faces of two cigarette rows in which n cigarettes are arranged in staggered rows with a cigarette row in which the (n−1) cigarettes are arranged intervening therebetween and a second line segment connecting centroid positions of filter end faces inwardly adjacent to the endmost filter end faces, and
   obtaining a distance difference between the first and second line segments and the centroid positions of the filter end faces located at both the ends of the (n−1) cigarette row, as a distance difference component in a direction of arrangement of the cigarettes between the centroid positions of the filter end faces.

16. A method for detecting an excess cigarette feeding error comprising the following steps:
   taking an inspection image of a filter end face of a cigarette bundle formed by stacking, in a staggered manner, cigarette rows each containing n filter cigarettes coaxially and horizontally arranged and cigarette rows each containing (n−1) filter cigarettes coaxially and horizontally arranged, from an axial direction of the cigarettes with a camera, and
   analyzing the inspection image, and further comprising:
   a first judging step comprising:
      detecting the number of the filter cigarettes of each of the cigarette rows on the basis of information about the shape of the filter end face, which is obtained from the inspection image, and
      judging that there is an excess feeding error when it is detected that the number of the cigarettes is more than a predetermined number in any one of the cigarette rows;
   a third judging step comprising:
      obtaining color information of the inside of an inspection window smaller than the filter end face of the cigarettes, which is set close to each end of the cigarette row in which (n−1) cigarettes are arranged in the inspection image, and
      judging that there is an excess feeding error when the color information indicates a color of the filters; and
   a fourth judging step comprising:
      finding from the inspection image centroid positions of endmost filter end faces of the cigarette row in which the n cigarettes are arranged and centroid positions of the filter end faces inwardly adjacent to the endmost filter end faces,
      finding a centroid position of a filter end face located at each end of a cigarette row in which the (n−1) cigarettes are arranged,
      judging a distance difference of these centroid positions, and
      judging that the cigarette row of the (n−1) cigarettes has an excess feeding error when the distance difference is large.

17. The method according to claim 16, wherein an excess feeding error is detected in the fourth judging step in parallel with the first and third judging steps or if there is no excess cigarette feeding error detected in the first and third judging steps.

18. The method according to claim 16, wherein the fourth judging step comprising:
   obtaining a first line segment connecting centroid positions of endmost filter end faces of two cigarette rows in which n cigarettes are arranged in staggered rows with a cigarette row in which the (n−1) cigarettes are arranged intervening therebetween and a second line segment connecting centroid positions of filter end faces inwardly adjacent to the endmost filter end faces, and
   obtaining a distance difference between the first and second line segments and the centroid positions of the filter end faces located at both the ends of the (n−1) cigarette row, as a distance difference component in a direction of arrangement of the cigarettes between the centroid positions of the filter end faces.

19. A method for detecting an excess cigarette feeding error comprising the following steps:
   taking an inspection image of a filter end face of a cigarette bundle formed by stacking, in a staggered manner, cigarette rows each containing n filter cigarettes coaxially and horizontally arranged and cigarette rows each containing (n−1) filter cigarettes coaxially and horizontally arranged, from an axial direction of the cigarettes with a camera, and
   analyzing the inspection image, and further comprising:
   a first judging step comprising:
      detecting the number of the filter cigarettes of each of the cigarette rows on the basis of information about the shape of the filter end face, which is obtained from the inspection image, and
      judging that there is an excess feeding error when it is detected that the number of the cigarettes is more than a predetermined number in any one of the cigarette rows;
   a second judging step comprising:
      finding from the inspection image a centroid position of each of the filter end faces in the cigarette row containing the (n−1) cigarettes,
      obtaining centroid-to-centroid distance between adjacent filter end faces, and
      judging that there is an excess feeding error when difference between a maximum value and a minimum value of the centroid-to-centroid distance is substantially equal to a previously-known diameter of the filter end face;
   a third judging step comprising:
      obtaining color information of the inside of an inspection window smaller than the filter end face of the cigarettes, which is set close to each end of the cigarette row in which (n−1) cigarettes are arranged in the inspection image, and
      judging that there is an excess feeding error when the color information indicates a color of the filters; and
   a fourth judging step comprising:
      finding from the inspection image centroid positions of endmost filter end faces of the cigarette row in which the n cigarettes are arranged and centroid positions of the filter end faces inwardly adjacent to the endmost filter end faces,
      finding a centroid position of a filter end face located at each end of a cigarette row in which the (n−1) cigarettes are arranged,
      judging a distance difference of these centroid positions, and
      judging that the cigarette row of the (n−1) cigarettes has an excess feeding error when the distance difference is large.

20. The method according to claim 19, wherein an excess feeding error is detected in the fourth judging step in parallel with the first to third judging steps or if there is no excess cigarette feeding error detected by in the first to third judging steps.

21. The method according to claim 19, wherein the fourth judging step comprising:
- obtaining a first line segment connecting centroid positions of endmost filter end faces of two cigarette rows in which n cigarettes are arranged in staggered rows with a cigarette row in which the (n−1) cigarettes are arranged intervening therebetween and a second line segment connecting centroid positions of filter end faces inwardly adjacent to the endmost filter end faces, and
- obtaining a distance difference between the first and second line segments and the centroid positions of the filter end faces located at both the ends of the (n−1) cigarette row, as a distance difference component in a direction of arrangement of the cigarettes between the centroid positions of the filter end faces.

\* \* \* \* \*